(12) United States Patent
Sloan et al.

(10) Patent No.: US 7,517,346 B2
(45) Date of Patent: Apr. 14, 2009

(54) RADIO FREQUENCY ABLATION SYSTEM WITH INTEGRATED ULTRASOUND IMAGING

(75) Inventors: Todd Sloan, Medway, MA (US); Isaac Ostrovsky, Wellesley, MA (US); Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 410 days.

(21) Appl. No.: 11/053,344

(22) Filed: Feb. 8, 2005

(65) Prior Publication Data

US 2006/0178665 A1 Aug. 10, 2006

(51) Int. Cl.
*A61B 18/14* (2006.01)
*A61B 8/12* (2006.01)
(52) U.S. Cl. .......................................... 606/41; 600/439
(58) Field of Classification Search ................. 607/101; 606/32, 41; 128/898; 600/439
See application file for complete search history.

(56) References Cited

U.S. PATENT DOCUMENTS

| | | | |
|---|---|---|---|
| 5,967,984 A | 10/1999 | Chu et al. | |
| 6,198,974 B1 * | 3/2001 | Webster, Jr. | 607/122 |
| 6,692,494 B1 | 2/2004 | Cooper et al. | |
| 6,704,605 B2 * | 3/2004 | Soltis et al. | 607/127 |
| 6,764,488 B1 | 7/2004 | Burbank et al. | |
| 7,195,629 B2 * | 3/2007 | Behl et al. | 606/41 |
| 2002/0002349 A1 | 1/2002 | Flaherty et al. | |

FOREIGN PATENT DOCUMENTS

WO 98/44857 10/1998

\* cited by examiner

*Primary Examiner*—Lee S Cohen
(74) *Attorney, Agent, or Firm*—Fay Kaplun & Marcin, LLP

(57) ABSTRACT

A tissue ablation system comprises a first electrode assembly adapted for insertion into a target tissue mass within a body, the first electrode assembly including a first electrode coupled to a source of RF energy in combination with an ultrasound imaging probe movably coupled to the first electrode assembly for insertion with the first electrode assembly to a desired location relative to the target tissue mass, the probe being movable relative to the first electrode assembly between an insertion configuration in which a distal end of the probe covers a distal end of the first electrode assembly and a deployed configuration in which the distal end of the first electrode assembly is uncovered. A method of ablating target tissue within a body comprises placing a distal dome of an ultrasound imaging probe in overlying alignment with a first cannula of an RF ablation device and inserting the probe and the RF ablation device through a lumen of an insertion device to a desired location adjacent to a target tissue mass in combination with moving the distal dome away from a distal end of the first cannula to expose a distal end thereof, inserting the distal end of the first cannula into the target tissue mass to position a first electrode of the RF ablation device at a first desired location within the target tissue mass, obtaining an image of the target tissue mass and the first electrode via the probe and applying RF energy to the target tissue mass via the first electrode.

32 Claims, 3 Drawing Sheets

RADIO FREQUENCY ABLATION SYSTEM WITH INTEGRATED ULTRASOUND IMAGING

BACKGROUND

Fibroids, tumors and other tissue masses are often treated by ablation. In many cases, local ablation of the diseased tissue is carried out by inserting a therapeutic device into the tissue and carrying out therapeutic activity designed to destroy the diseased cells. For example, electrical energy may be applied to the affected area by placing one or more electrodes into the affected tissue and discharging electric current therefrom to ablate the tissue. Alternatively, tissue may be ablated cryogenically, by applying heat or chemically by injecting fluids with appropriate properties to the target tissue.

However, as many tumors and fibroids are loosely held in place by ligaments and other structures, movement of the target tissue mass may make it difficult to insert a needle electrode or other energy delivery device thereinto. Grasping devices and anchors may be used to immobilize the target tissue mass while an electrode is inserted thereinto, but these procedures add more complexity to the operation and may require additional incisions. The surgeon may also require assistance from additional personnel to carry out such procedures.

RF ablation procedures also benefit from visualization methods used to correctly position the electrodes within the target tissue mass and to determine the effectiveness of treatment. A degree of visualization may be obtained by inserting the ablation device into the vicinity of the target tissue mass using an endoscopic instrument with a vision system. However, the field of view of these vision systems is small and may be insufficient to properly perform and assess the effectiveness of the treatment. Conventional vision systems may also have difficulty in facilitating the positioning of the electrodes within the tissue, as the tissue itself obscures viewing of the electrodes.

SUMMARY OF THE INVENTION

In one aspect, the present invention is directed to a tissue ablation system comprising a first electrode assembly adapted for insertion into a target tissue mass within a body, the first electrode assembly including a first electrode coupled to a source of RF energy in combination with an ultrasound imaging probe movably coupled to the first electrode assembly for insertion with the first electrode assembly to a desired location relative to the target tissue mass, the probe being movable relative to the first electrode assembly between an insertion configuration in which a distal end of the probe covers a distal end of the first electrode assembly and a deployed configuration in which the distal end of the first electrode assembly is uncovered.

The present invention is further directed to a method of ablating target tissue within a body comprising placing a distal dome of an ultrasound imaging probe in overlying alignment with a first cannula of an RF ablation device and inserting the probe and the RF ablation device through a lumen of an insertion device to a desired location adjacent to a target tissue mass in combination with moving the distal dome away from a distal end of the first cannula to expose a distal end thereof, inserting the distal end of the first cannula into the target tissue mass to position a first electrode of the RF ablation device at a first desired location within the target tissue mass, obtaining an image of the target tissue mass and the first electrode via the probe and applying RF energy to the target tissue mass via the first electrode.

DETAILED DESCRIPTION

Figure 1:
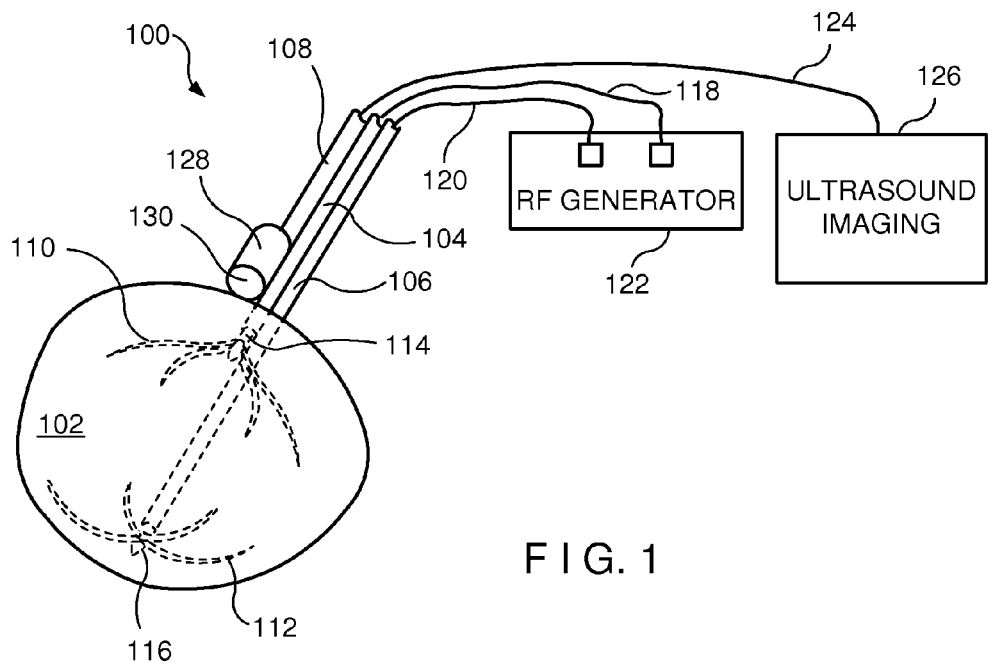
FIG. 1 is a perspective view showing an embodiment of the ablation device according to the present invention.

The present invention may be further understood with reference to the following description and the appended drawings, wherein like elements are referred to with the same reference numerals. The present invention relates to devices for treating tissue such as fibroids, tumors and other tissue masses by applying electric energy through electrodes inserted into a target tissue mass. The present invention also relates to devices used to ablate tissue to reshape an organ.

In one embodiment, energy delivery elements of the apparatus according to the present invention are deployable from a single medical instrument. For example, such a single instrument may include two tined arrays or one tined array and one clamp which are placed on or within the target tissue mass to treat the target tissue. In other embodiments, the instrument may include devices for grasping and holding in place the target tissue mass, minimizing the minimum number of incisions and medical personnel required to perform the procedure.

Conventional systems for treating target tissue such as a tumor or fibroid with needle-based radio frequency (RF) devices include, for example, the LeVeen Needle Electrode™ from the Oncology Division of Boston Scientific Corp. and the Starburst™ product line available from RITA Medical Systems, Inc. When using these devices, the surgeon punctures the target tissue mass with the device's needle and then deploys one or more RF tines into the tissue mass. An electric voltage is then applied to the tines to necrose the target tissue so that it is ablated. Lower levels of energy may be applied to achieve other therapeutic goals on the target tissue.

As described above, these devices are most effectively used on their own only by highly skilled individuals as it is difficult to properly place such devices within target tissue masses which tend to move when contacted. Even with skilled practitioners, multiple attempts may be required before a needle is correctly positioned. Alternatively, grasping devices such as tumor screws may be used in conjunction with these devices to immobilize and apply traction to the target tissue mass during insertion of the needle. However, this requires more time (or additional personnel) and may require multiple entry points through the skin, further increasing the complexity, time required for and discomfort associated with the procedure. As would be understood by those skilled in the art, if the electrodes are not placed sufficiently close to a desired location within the target tissue mass, the targeted tissue may not be treated as desired as the range of RF ablation is limited. In addition, misplaced electrodes may damage non targeted tissue in proximity to the target tissue mass. Although ultrasonic monitoring devices may be used to correctly place the electrodes in the target tissue, the quality of the images depends on the size of the probe's distal dome and there has been a trade-off between image quality and the invasiveness of the procedure. In addition, the size of ultrasound probes which have been employed has been limited by the size of the working channels of the devices through which these probes have been inserted to the target tissue mass.

FIG. 1 shows an exemplary embodiment of a bipolar RF ablation system with an integrated ultrasound imaging probe, according to the invention. The system is designed and configured so that it can be inserted into the patient's body through a small access port or channel, similar to a trocar. In this manner, the system can be used to perform minimally invasive treatments, such as laparoscopically guided RF ablation of uterine fibroids. Other types of fibroids or abnormal tissues may also be treated with the exemplary system, particularly those formed in the lumens of hollow organs. It will be apparent to those of skill in the art that other procedures may also be carried out with the device according to the invention. For example, target tissues may be reshaped by ablation or resection, and other therapeutic goals may be achieved by delivering selected amounts of energy to the target tissue.

An RF ablation system 100 according to an exemplary embodiment of the invention comprises an RF portion having two cannulas 104, 106 and an integrated imaging portion having an imaging device shaft 108. The system is configured to fit through a small port, through a trocar-like insertion device, or though the working channel of an endoscope to perform minimally invasive procedures. For example, an exemplary system may fit through openings less than 10 mm in diameter and may more preferably fit through openings less than 5 mm in diameter. RF ablation cannulas 104, 106 are shown in a side by side configuration, extending along parallel axes. The cannulas 104, 106 are extendable side by side, independently from one another, so that the distal end of each cannula may be positioned at a different desired site within a target tissue mass 102. For example, a sharp distal end 114 of the RF cannula 104 may be inserted and positioned at one end of the target tissue mass 102 just inside a surface thereof while the sharp distal end 116 of the RF cannula 106 is inserted further into the target tissue mass 102 to a location at the opposite end of the target tissue mass 102. Thus, an ablation region of desired dimensions may be created by properly positioning the two distal ends 114, 116 relative to one another.

After the RF cannulas 104, 106 have been inserted within the target tissue mass 102, arrays of tines, or electrodes, may be deployed independently therefrom to better define the ablation region to be treated. For example, a first array of tines 110 may be deployed from an opening at the distal end 114 and a second array of tines 112 may be deployed from the second distal end 116. As would be understood by those skilled in the art, the arrays 110, 112 are preferably shaped to define a size and shape of a region of the target tissue mass 102 to be ablated. Connections 118, 120 convey the RF energy from a generator 122 to each of the arrays 110, 112 with the polarity of the energy provided to the array 110 being opposite that provided to the array 112 to create a bipolar ablation device. Connections 118, 120 may be electric wires, or other types of electric connections used conventionally in RF ablation probes.

The configuration of the RF ablation system according to the invention may be used to treat target tissues of different dimensions, simply by varying the relative positions of arrays 110, 112 within the target tissue mass 102. The system also allows for staged ablation of the target tissue mass 102, thus enabling the operator to ablate a larger volume of tissue in one operation. For example, a first region of the target tissue mass 102 may be treated with the arrays 110, 112 relatively close to one another. The arrays 110, 112 may then be moved further apart, to treat a second, larger region of the target tissue mass 102. The repositioning and treatment steps may be further repeated as needed to treat the entire target tissue mass 102.

The ultrasound visualization portion of the exemplary device shown in FIG. 1 includes an ultrasound probe comprising a shaft 108 which is placed side by side with the two RF cannulas 104, 106. The RF cannulas 104, 106 can be moved longitudinally relative to the shaft 108, but are attached thereto to form an integrated unit. The ultrasound probe also includes a dome 128 with a forward facing transducer 130 designed to be introduced into the body in the vicinity of the target tissue mass 102. The shaft 108 has a smaller diameter than the dome 128, to reduce the cross sectional area of the device. In addition, the dome 128 is mounted on the shaft 108 offset from an axis thereof. The assembly of the shaft 108 and the dome 128 can be rotated along the longitudinal axis, so that the dome 128 can be rotated toward and away from the RF cannulas 104, 106.

Figure 2:
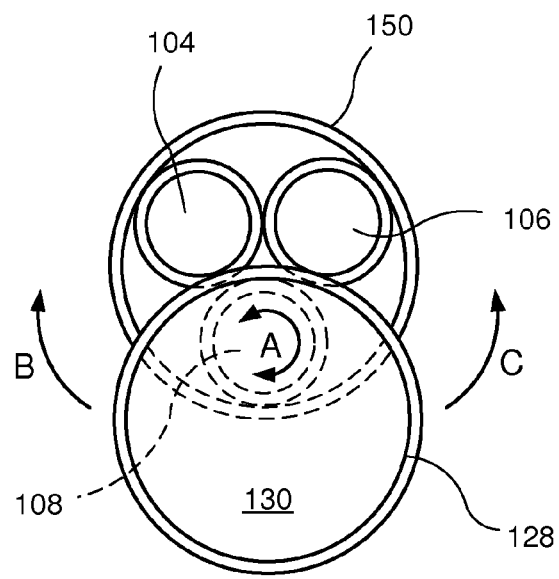
FIG. 2 is a front view showing the ablation device of FIG. 1.
Figure 3:
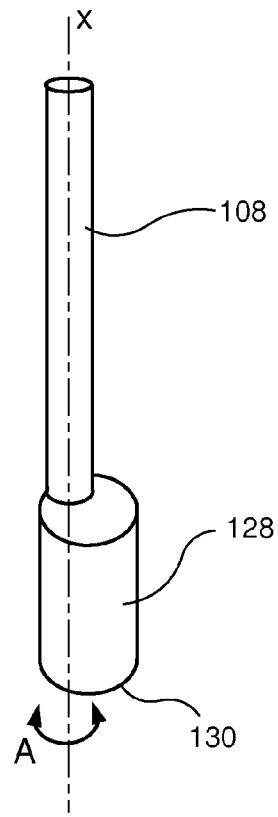
FIG. 3 is a perspective view of an ultrasound probe according to the present invention.

According to the present invention, the dome 128 containing the ultrasound sensor transducer 130 is rotatable along the longitudinal axis of the shaft 108. As depicted in greater detail in the front and perspective views shown in FIGS. 2 and 3, the dome 128 rotates about the centerline axis x of the shaft 108. Since the dome 128 is offset relative to the shaft 108, and since the shaft 108 is generally aligned with the distal portions of cannulas 104, 106, it is possible to place the dome 128 in front of or beside the distal ends 114, 116 thereof. Specifically, when the shaft 108 is rotated as shown by the arrows A, the dome 128 swings along one of the paths shown by the arrows B and C. FIG. 2 shows the dome 128 in an operative position, to the side of the cannulas 104, 106. In the operative position, the dome 128 is moved away from and does not interfere with the openings at the distal ends 114, 116 so that deployment of the array of tines 110, 112 from the cannulas 104, 106 is unrestricted. At the same time, the operative position provides the dome 128 with an unobstructed view of an operative field forward of the transducer 130.

When the shaft 108 is rotated approximately 180 degrees in either direction from the orientation shown in FIG. 2, the dome 128 is positioned in front of the openings 114, 116, in an insertion/removal configuration. This configuration facilitates passage of the dome 128 to and from the target tissue mass by reducing the profile of the entire device. When the dome 128 is placed in front of the cannulas 104, 106, the overall cross sectional area of the ablation system device 100 is reduced to a minimum. By properly selecting the geometry of the shaft 108 and of the dome 128, the cross sectional area of the device 100 in the insertion configuration may be limited to the cross sectional area of the dome 128 with the width of the cannulas 104, 106 and of the shaft 108 shadowed behind the width of the distal dome 128.

In the insertion configuration, the size of the dome 128, and thus of the transducer 130, is the limiting factor which determines whether the RF ablation device 100 can pass through a particular insertion lumen. In this configuration, the profile dimensions of the cannulas 104, 106 and of the shaft 108 are all contained within the profile dimension of the distal dome 128. The profile dimension corresponds to the maximum width of the device as seen from the front as the RF device is introduced into a lumen of an endoscope, trocar, or other insertion device. According to the invention, the width of the dome 128 is at least as great as that of the rest of the device. The dome 128 can thus be selected to be as large as will fit through the insertion device.

In one exemplary embodiment, the dome 128 is dimensioned to contain an ultrasound transducer capable of operating approximately in the 5 to 8 MHz frequency range. This frequency range is desirable because it provides higher resolution images of biological structures surrounding the transducer. Although ultrasonic transducers utilizing lower frequencies may obtain higher quality images these transducers also require larger dimension domes. By providing a dome 128 which at least as large as the shaft 108, and which is offset relative to the axis of the shaft 108, the device according to embodiments of the present invention allow the dimensions of the transducer to be maximized. An imaging station 126 may be connected to the transducer 130 via an electric connection 124 which may include, for example, electric wires, a wireless connection, optical connections or other conventional means.

Figure 4:
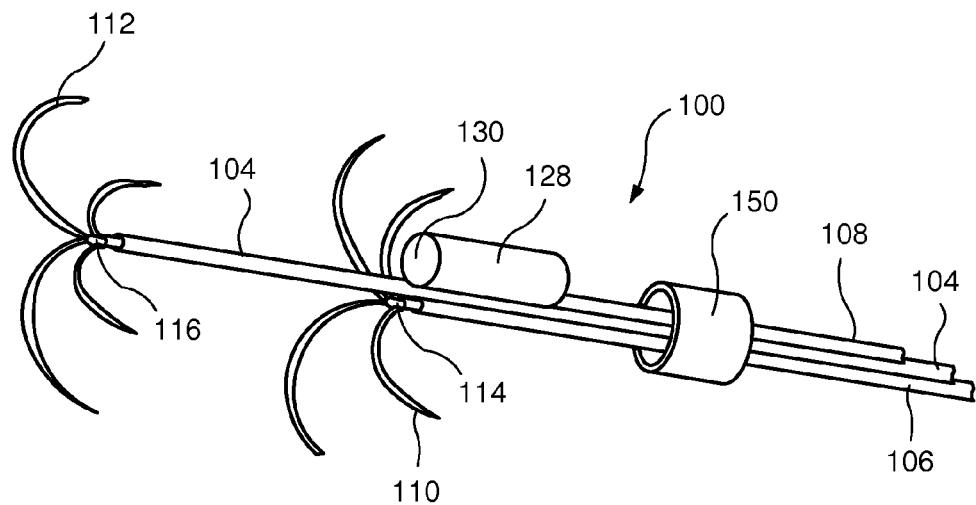
FIG. 4 is a perspective view of the ablation device of FIG. 1, with an insertion device.

As described above, when in the insertion configuration, the large dome 128 is rotated in front of the cannulas 104, 106, so that the entire RF ablation system 100 can fit through a small passage, such as a working channel of an endoscope or of a trocar-like tube 150. Once the dome 128 has exited a distal end of the tube 150, the dome 128 is rotated away from the cannulas 104, 106 to expose distal openings thereof so that the arrays of tines 110, 112 may be deployed therefrom. FIG. 4 shows an exemplary embodiment of the RF ablation system 100 in the deployed configuration, with arrays of tines 110, 112 deployed and the dome 128 rotated away from cannulas 104, 106. When the procedure has been completed, the arrays of tines 110, 112 are retracted and the dome 128 is rotated back into the insertion/removal configuration and the device is withdrawn proximally through the tube 150.

Figure 5:
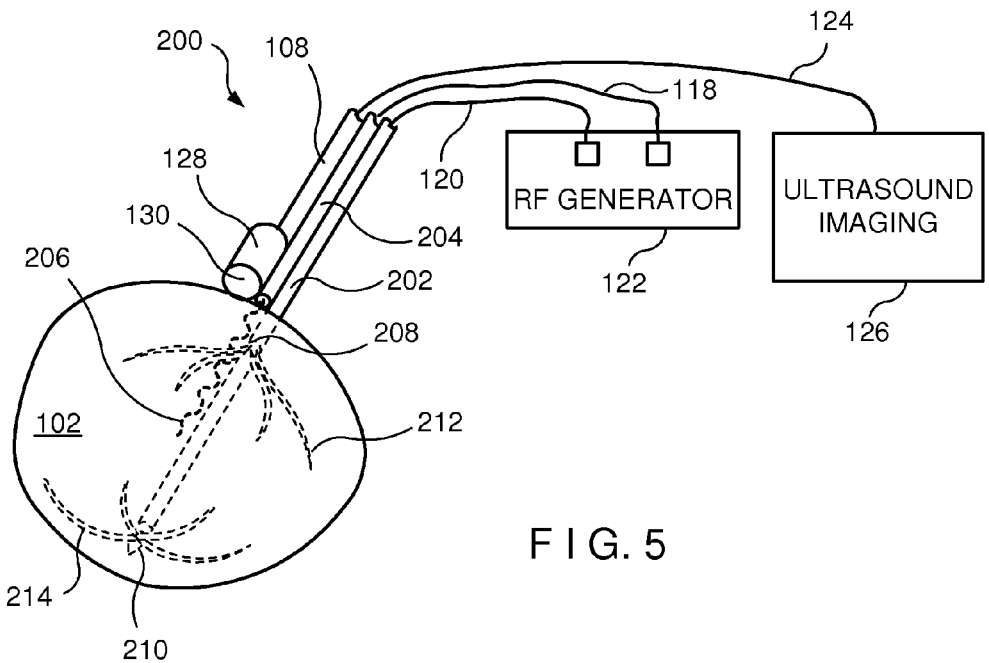
FIG. 5 is a perspective view of another embodiment of the ablation device according to the present invention.
Figure 6:
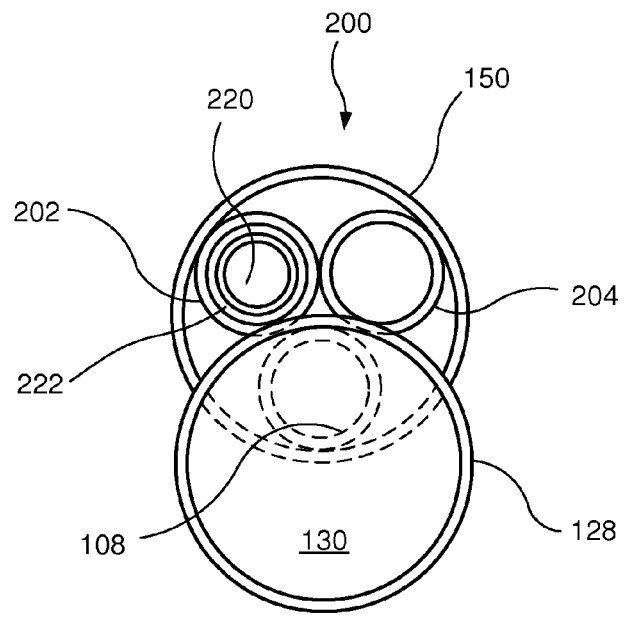
FIG. 6 is a front view showing the ablation device of FIG. 5.

FIGS. 5 and 6 show an RF ablation system 200 according to a second exemplary embodiment of the invention. A visualization portion of the RF ablation system 200 includes a shaft 108 and a dome 128 analogous to those described with reference to FIG. 1. As with the system 100 of FIG. 1, the dome 128 is offset relative to the shaft 108 and can be rotated away from and toward two cannulas 202, 204 between an insertion/removal configuration and a deployed configuration. The cannula 202 is a dual lumen cannula including first and second lumens 220, 222 through which arrays of tines 212 and 214 are deployed. As shown in FIG. 6, the lumens 220, 222 are preferably concentric with each allowing passage of one of the two arrays of tines 212, 214. Alternatively, the lumens 220, 222 may be formed in a side-by-side or top-bottom arrangement. In the concentric arrangement, exit openings 208 are formed at one or more selected locations along the length of the cannula 202, so that the array of tines 212 may be deployed through the wall separating the lumens 220, 222 at the selected locations relative to the location (e.g., opening 210 at the distal end of the cannula 202) from which the array of tines 214 is deployed.

The system 200 may further include a second cannula 204 through which a tissue anchoring device (e.g., a tissue screw 206) may be deployed. The cannula 204 may be fixed or movable relative to the cannula 202 and the shaft 208, depending on the requirements of the system. For example, the cannula 204 may be inserted through the tube 150 until its distal end is in a desired position adjacent to the target tissue mass 102. The tissue anchoring element 206 may then be deployed therefrom to retain the target tissue mass 102 in a desired position relative to the RF ablation system 200 (e.g., by grasping the target tissue mass 102) while the cannula 202 is inserted thereinto. The tubes forming the lumens 220, 222 may then be manipulated so that openings 208, 210 are placed in desired positions relative to the target tissue mass 102. The correct positioning of the arrays may be ascertained using visualization provided by the ultrasound transducer 130. The RF ablation procedure may then take place as described above with visualization of the tissue providing feedback which the operator may use to determine when a desired degree of treatment of the target tissue mass 102 has been achieved.

As described above, as the RF ablation system 200 is initially inserted into the patient through a tube 150, the cannulas 202, 204 are maintained in the withdrawn position, behind the dome 128 which is maintained in the insertion/removal configuration—i.e., with the dome 128 rotated to cover the cannulas 202, 204, minimizing the cross sectional profile of the device. Once the RF ablation system 200 has been located in a desired position adjacent to the target tissue mass 102, the dome 128 is rotated away from the cannulas 202, 204 to the deployed configuration, the tissue anchoring device 206 is extended to grasp the target tissue mass 102 and the cannula 202 is extended into the target tissue mass 102. Thereafter, the openings 208, 210 are located in desired positions within the target tissue mass 102 and the arrays of tines 212, 214 are deployed for tissue ablation. As described above, when the desired degree of treatment has been completed, the arrays of tines 212, 214 are retracted into the lumens 220, 222, respectively, the tissue grasping device 206 is withdrawn into the cannula 204 and the cannulas 202 and 204 are withdrawn into the tube 150. Then the dome 128 is rotated back into the insertion/removal configuration and the system 200 is withdrawn from the body via the tube 150.

Figure 7:
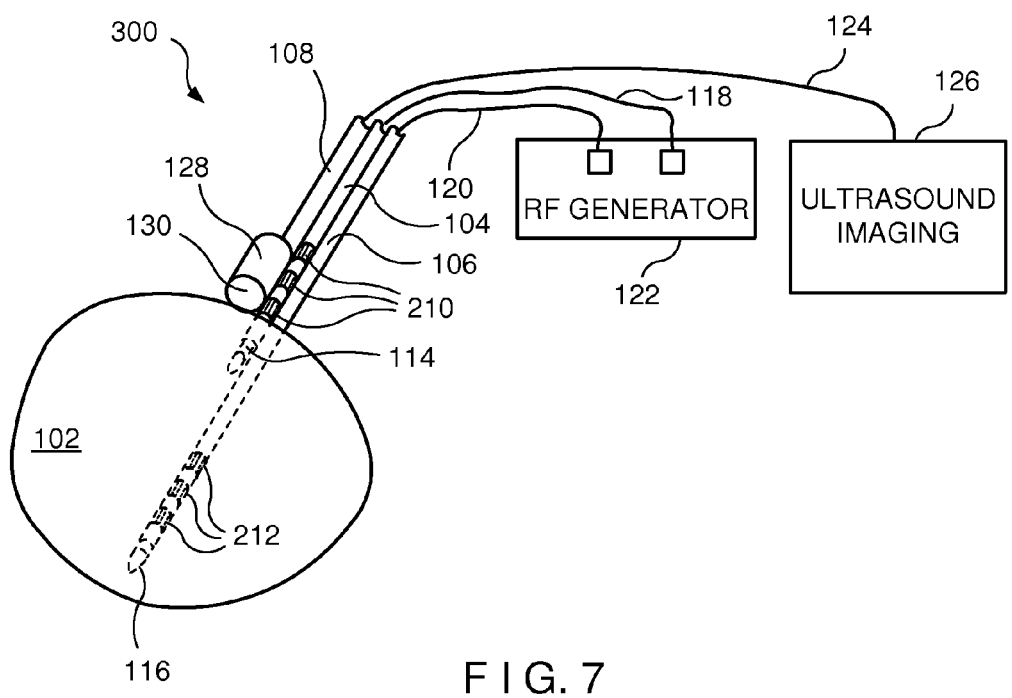
FIG. 7 is a perspective view of another embodiment of the ablation device according to the present invention.

FIG. 7 shows another exemplary embodiment of an RF ablation system 300 according to the present invention. The ablation system 300 is substantially similar to the prior embodiments in construction and operation except for the construction of the electrodes 210, 212. As opposed to the arrays of tines in the previous embodiments, the system 300 includes electrodes 210, 212 formed as conductive bands around the first and second cannulas 104, 106, respectively. Those skilled in the art would understand that each of the electrodes 210, 212 may comprise one or more conductive bands which may be energized singularly or in any combinations desired.

The present invention has been described with reference to specific exemplary embodiments. Those skilled in the art will understand that changes may be made in details, particularly in matters of shape, size, material and arrangement of parts. For example, those skilled in the art will understand that above described bipolar RF ablation system could be replaced by a monopolar RF ablation system with only a single electrode inserted into the body. That is, those skilled in the art will understand that a monopolar RF ablation system could be formed including an ultrasound element movable between an insertion/removal configuration minimizing a profile of the system and a deployed condition in which a field of view of the ultrasound is unobstructed by a single electrode and does not interfere with deployment of this single electrode. Accordingly, various modifications and changes may be made to the embodiments. Additional or fewer components may be used, depending on the condition that is being treated using the described RF ablation system and devices. The specifications and drawings are, therefore, to be regarded in an illustrative rather than a restrictive sense.

What is claimed is:

1. A tissue ablation system, comprising:
 a first electrode assembly adapted for insertion into a target tissue mass within a body, the first electrode assembly including a first electrode coupled to a source of RF energy; and
 an ultrasound imaging probe movably coupled to the first electrode assembly for insertion with the first electrode assembly to a desired location relative to the target tissue mass, the probe being movable rotatably relative to the first electrode assembly between an insertion configuration in which a distal end of the probe covers a distal end of the first electrode assembly and a deployed configuration in which the distal end of the first electrode assembly is uncovered.

2. The tissue ablation system according to claim 1, wherein the probe includes a dome coupled to a distal end of the shaft, the dome being offset relative to an axis of the shaft, and wherein the shaft is rotatable about the axis to move the probe between the configurations.

3. The tissue ablation system according to claim 1, wherein the first electrode assembly includes a first cannula, the first electrode being deployable from the first cannula after the first cannula has penetrated the target tissue mass.

4. The tissue ablation system according to claim 3, further comprising a second electrode assembly a distal end of which, when the probe is in the insertion configuration, is covered by the probe, the second electrode assembly being adapted for insertion into the target tissue mass and including a second electrode coupled to the source of RF energy, the second electrode assembly further including a second cannula, the second electrode being deployable from the second cannula after the second cannula has penetrated the target tissue mass.

5. The tissue ablation system according to claim 4, wherein the first and second electrodes comprise first and second deployable arrays of tines, respectively.

6. The tissue ablation system according to claim 5, wherein the first array of tines is deployable from a distal opening of the first cannula and the second array of tines is deployable from a distal opening of the second cannula.

7. The tissue ablation system according to claim 4, wherein the second cannula is extendable independently of the first cannula.

8. The tissue ablation system according to claim 4, wherein, when in the insertion configuration, a distal portion of the probe overlies distal ends of the first and second cannulas.

9. The tissue ablation system according to claim 8, wherein, when in the insertion configuration, radially outermost portions of the first and second cannulas are contained within a profile dimension of the distal portion of the probe.

10. The tissue ablation system according to claim 4, further comprising a tissue anchor cannula connected substantially side by side to the first cannula.

11. The tissue ablation system according to claim 10, further comprising a tissue anchoring screw extendable from the tissue anchor cannula.

12. The tissue ablation system according to claim 1, wherein, when in the operative configuration, the probe does not interfere with extension of the first electrode into the target tissue mass.

13. The tissue ablation system according to claim 1, wherein the first cannula is extendable longitudinally relative to the probe.

14. The tissue ablation system according to claim 1, further comprising an ultrasound imaging station operatively connected to the probe.

15. The tissue ablation system according to claim 1, wherein the first electrode assembly includes a first cannula, the first electrode being a plurality of conductive bands formed around the first cannula.

16. The tissue ablation system according to claim 15, further comprising a second electrode assembly further including a second cannula, the second electrode assembly including a second electrode, the second electrode being a plurality of conductive bands formed around the second cannula.

17. A method of ablating target tissue within a body, comprising:
 placing a distal dome of an ultrasound imaging probe in overlying alignment with a first cannula of an RF ablation device;
 inserting the probe and the RF ablation device through a lumen of an insertion device to a desired location adjacent to a target tissue mass;
 moving the distal dome away from a distal end of the first cannula to expose a distal end thereof;
 inserting the distal end of the first cannula into the target tissue mass to position a first electrode of the RF ablation device at a first desired location within the target tissue mass;
 obtaining an image of the target tissue mass and the first electrode via the probe; and
 applying RF energy to the target tissue mass via the first electrode.

18. The method according to claim 17, wherein the RF ablation device further comprises a second cannula, the method further comprising inserting the second cannula into the target tissue mass to position a second electrode at a second desired location, wherein the probe overlies the distal end of the second cannula as the probe and the RF ablation device are inserted through the lumen of the insertion device.

19. The method according to claim 18, further comprising deploying the first electrode from the first cannula and deploying the second electrode from the second cannula after the first and second cannulas have attained the first and second desired locations, respectively.

20. The method according to claim 18, wherein the first and second cannulas and the probe are simultaneously inserted through the lumen of the insertion device.

21. The method according to claim 17, wherein placing the distal dome in overlying alignment with the first cannula limits a profile dimension of the RF ablation device to a profile dimension of the distal dome.

22. The method according to claim 17, wherein the RF ablation device further comprises a tissue anchor cannula, the method further comprising deploying a tissue anchoring device from the tissue anchor cannula after the distal dome has been moved away from the distal end of the first cannula, wherein the distal dome overlies the tissue anchor cannula as the probe and the RF ablation device are inserted through the lumen of the insertion device and moving the distal dome to expose the distal end of the first cannula exposes a distal end of the tissue anchor cannula.

23. The method according to claim 17, further comprising deploying the first electrode from the first cannula after inserting the distal end of the first cannula to the first desired location.

24. The method according to claim 17, further comprising monitoring the ablation of the target tissue with the ultrasound imaging probe.

25. The method according to claim 17, wherein the probe employs ultrasound in a frequency of between about 5 MHz and about 8 MHz.

26. An RF ablation probe with integrated ultrasound sensor, comprising:
- a first cannula deploying a first electrode through a first distal opening thereof;
- a shaft connected substantially side by side with the first cannula; and
- a dome containing an ultrasound transducer coupled to a distal end of the shaft, the dome being offset relative to a longitudinal axis of the shaft, wherein the shaft is rotatable about the longitudinal axis to move the dome between an insertion configuration overlying the first distal opening and an operative configuration exposing the first distal opening.

27. The RF ablation probe according to claim 26, wherein the first cannula is extendable independently of the shaft.

28. The RF ablation probe according to claim 26, wherein the shaft and the first cannula are insertable jointly through a lumen of an insertion device.

29. The RF ablation probe according to claim 26, further comprising a second electrode deployable through a proximal opening formed in the first cannula.

30. The RF ablation probe according to claim 26, further comprising a second RF cannula connected substantially side by side with the first cannula and a second electrode deployable through a distal opening of the second cannula.

31. The RF ablation probe according to claim 26, wherein the ultrasound transducer operates in a frequency range of between about 5 MHz and about 8 MHz.

32. The RF ablation probe according to claim 26, wherein the dome has a maximum profile dimension less than 5.0 mm.

* * * * *